US009638619B2

(12) United States Patent
Yamaguchi (10) Patent No.: US 9,638,619 B2
(45) Date of Patent: May 2, 2017

(54) OPTICAL ANALYSIS CELL AND PARTICLE SIZE DISTRIBUTION MEASURING APPARATUS

(71) Applicant: HORIBA, Ltd., Kyoto-shi, Kyoto (JP)

(72) Inventor: Tetsuji Yamaguchi, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 14/995,685

(22) Filed: Jan. 14, 2016

(65) Prior Publication Data
US 2016/0223454 A1     Aug. 4, 2016

(30) Foreign Application Priority Data

Jan. 30, 2015    (JP) ................................. 2015-017491

(51) Int. Cl.
| | |
|---|---|
| *G01N 1/10* | (2006.01) |
| *G01N 15/02* | (2006.01) |
| *G01N 15/00* | (2006.01) |

(52) U.S. Cl.
CPC . *G01N 15/0211* (2013.01); *G01N 2015/0053* (2013.01)

(58) Field of Classification Search
CPC ............... G01N 21/03; G01N 21/0303; G01N 2021/0307; G01N 2021/0321; G01N 2021/0375; G01N 2021/0378; G01N 2021/0382; G01N 2021/0389; G01N 2015/1493; G01N 15/1404; G01N 15/1436

(Continued)

(56) References Cited

U.S. PATENT DOCUMENTS

| | | | | |
|---|---|---|---|---|
| 5,245,189 A | * | 9/1993 | Satoh ................. | G01N 21/3563 250/343 |
| 2011/0299067 A1 | * | 12/2011 | Yokoyama ............. | G01N 21/05 356/213 |
| 2012/0035061 A1 | * | 2/2012 | Bransky ............... | G01N 15/147 506/7 |

FOREIGN PATENT DOCUMENTS

| | | |
|---|---|---|
| EP | 0503934 A2 | 9/1992 |
| GB | 2341925 A | 3/2000 |

(Continued)

OTHER PUBLICATIONS

Search Report dated May 24, 2016; Patent Application No. GB1601291.6; total of 3 pages.

*Primary Examiner* — Sunghee Y Gray
(74) *Attorney, Agent, or Firm* — Lucas & Mercanti, LLP (57) ABSTRACT

The present invention is made focusing on the viscoelasticity of a sample, which is completely different from a conventional idea, and provides an optical analysis cell 100 that in order to easily make the thickness of the sample X uniform as well as making a pair of light transmitting plates 10 parallel to each other without the use of any spacer, includes the pair of light transmitting plates 10 that sandwich and hold the sample X having predetermined viscoelasticity between mutually opposed inward surfaces 10*a*. In addition, the optical analysis cell 100 further includes a distance fixing member 20 having a pair of opposed surfaces 21*a* and 22*a* provided separately from each other by a predetermined distance. Also, it is configured that the respective light transmitting plates 10 receive the elastic force of the sample X, and thereby outward surfaces 10*b* on the sides opposite to the inward surfaces 10*a* of the respective light transmitting plates 10 are pressed against corresponding respective opposed surfaces 21*a* and 22*a* to fix the separation distance between the inward surfaces 10*a*.

9 Claims, 10 Drawing Sheets

(58) Field of Classification Search
USPC .......................................................... 356/246
See application file for complete search history.

(56) References Cited

FOREIGN PATENT DOCUMENTS

| | | |
|---|---|---|
| JP | S63269042 A | 11/1988 |
| JP | H08178825 A | 7/1996 |
| JP | 09-072841 A | 3/1997 |

\* cited by examiner

OPTICAL ANALYSIS CELL AND PARTICLE SIZE DISTRIBUTION MEASURING APPARATUS

CROSS REFERENCE TO RELATED APPLICATION

This application claims the priority of Japanese Patent Application No. 2015-017491 filed on Jan. 30, 2015, which is incorporated by reference herein.

TECHNICAL FIELD

The present invention relates to an optical analysis cell and a particle size distribution measuring apparatus using the optical analysis cell.

BACKGROUND ART

In the past, analysis using a particle size distribution measuring apparatus has been performed after diluting a sample with a solvent to obtain concentration exhibiting a predetermined transmittance. However, depending on a sample, the sample may be condensed or dissolved by dilution and lead to a change in state, and therefore there is a demand to measure the sample in an original undiluted state.

In order to measure a sample in an original undiluted state, it is necessary to use a cell having a short optical path length so as to make the sample have a predetermined transmittance. However, an undiluted sample often has high concentration and high viscosity, and therefore it is difficult to put the sample into a cell, and also clean the cell.

For this reason, in the past, by interposing a spacer between a pair of light transmitting plates, and sandwiching a sample between the pair of light transmitting plates, the thickness of the sample has been made uniform.

For example, Patent Literature 1 describes an optical analysis cell that includes a pair of glass plates and is configured by putting a sample into a concave part formed in one of the glass plates and then superposing the other glass plate on the one glass plate.

In the above-described configuration, this optical analysis cell is adapted to make the thickness of the sample equal to the depth of the concave part, and the thickness of the sample can be made seemingly uniform without the use of any spacer. However, in truth, the optical analysis cell is based on completely the same idea as the above-described conventional idea.

Figure 1:
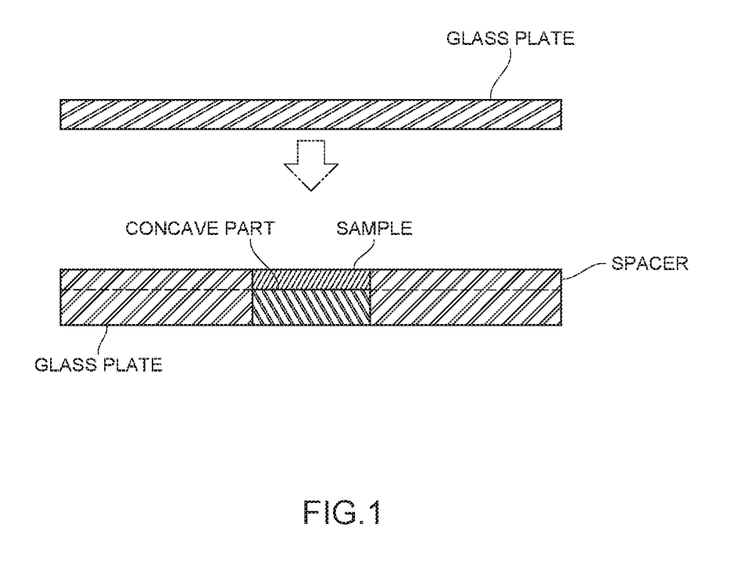
FIG. 1 is a diagram schematically illustrating the configuration of a conventional optical analysis cell.

This is because as illustrated in FIG. 1, the thickness of the sample is determined by the thickness of a part around the concave part of the one glass plate, and the part can be regarded as a spacer.

In addition, in the above-described configuration, in the case where the amount of the sample is larger than the volume of the concave part, when superposing the two glass plates on each other, part of the sample protrudes from the concave part, and the protruding sample gets between the two glass plates. As a result, the two glass plates cannot be made parallel, and light cannot pass straight through them, giving rise to the problem that an optical axis cannot be accurately adjusted.

On the other hand, in the case where the amount of the sample is smaller than the volume of the concave part, the concave part cannot be filled with the sample, and therefore the thickness of the sample cannot be made uniform.

As described, the above-described optical analysis cell is not practical at all because in order to make the glass plates parallel to each other while making the thickness of the sample uniform, it is necessary to make adjustments so as to make the amount of the sample equal to the volume of the concave part.

Further, in addition to the above-described optical analysis cell, there is another optical analysis cell that is formed by interposing an elastic spacer between two light transmitting plates and configured to be able to utilize the repulsive force of the spacer to adjust the separation distance and parallelism between the light transmitting plates by pushing one of the light transmitting plates with multiple screws.

However, in the above-described configuration, only adjusting the separation distance between the light transmitting plates so as to make the thickness of a sample uniform is very delicate work. In addition, making adjustments so as to make the two glass plates parallel to each other is extremely difficult.

CITATION LIST

Patent Literature

Patent Literature 1: JP-A-9-72841

SUMMARY OF INVENTION

Technical Problem

On the other hand, the present invention focuses on the viscoelasticity of a sample, which is completely different from the conventional idea, and a main object thereof is to provide an optical analysis cell that without the use of any spacer, makes it possible to easily make the thickness of the sample uniform as well as making a pair of light transmitting plates parallel to each other.

Solution to Problem

That is, the optical analysis cell according to the present invention is an optical analysis cell including a pair of light transmitting plates that sandwich and hold a sample having predetermined viscoelasticity between mutually opposed inward surfaces. Also, the optical analysis cell includes a distance fixing member having a pair of opposed surfaces provided separately from each other by a predetermined distance. Further, it is configured that the respective light transmitting plates receive the elastic force of the sample, and thereby outward surfaces on the sides opposite to the inward surfaces of the light transmitting plates are pressed against corresponding opposed surfaces to fix the separation distance between the inward surfaces.

In the optical analysis cell configured as described, since it is configured that the respective light transmitting plates receive the elastic force of the sample, and thereby the respective outward surfaces are pressed against the corresponding opposed surfaces to fix the separation distance between the inward surfaces, completely differently from the conventional idea, without the use of any spacer, it is easily possible to make the thickness of the sample uniform as well as making the pair of light transmitting plates parallel to each other.

Also, since it is configured to simply sandwich the sample between the pair of light transmitting plates, by pressing and lengthening the sample between the light transmitting plates without adjusting a sample amount, the thickness can be made uniform, and also the pair of light transmitting plates can be made parallel to each other, which is also superior in practicality.

It is preferable that around a sample holding space formed between the inward surfaces, a sample escape space is formed.

Such a configuration makes it possible to prevent the sample from unexpectedly flowing out of the optical analysis cell, and also surely make the thickness of the sample uniform because even if part of the sample protrudes from the sample holding space when sandwiching the sample between the light transmitting plates, the protruding sample flows into the sample escape space.

Although in the case where the light transmitting plates are fragile, they are required to be often replaced, in order to use inexpensive general-purpose products as the light transmitting plates, it is preferable that the respective light transmitting plates are flat plates.

In order to surely make the pair of light transmitting plates parallel to each other, it is preferable that the pair of opposed surfaces are provided parallel to each other.

As a specific embodiment, it is preferable that the distance fixing member has: a first holding body having one of the opposed surfaces; a second holding body having the other one of the opposed surfaces; and a connecting member that connects the holding bodies to each other.

In the above-described configuration, since the pair of opposed surfaces are respectively formed on the separate holding bodies, as compared with the case where the pair of opposed surfaces are formed on a single member, assembly work can be simplified.

It is preferable that at least one of the holding bodies has a guide part that guides an outward surface of a light transmitting plate to a corresponding opposed surface.

The above-described configuration makes it possible to prevent the respective light transmitting plates from being displaced in a planar direction when pressing the outward surfaces of the respective light transmitting plates against corresponding opposed surfaces.

It is preferable that at least one of the holding bodies is formed with a spot facing part formed by hollowing a surface opposed to the other one of the holding bodies.

The above-described configuration makes it possible to easily assemble the optical analysis cell by fitting the light transmitting plates into the spot facing part formed in the one holding body, and then blocking the spot facing part by the other holding body.

Also, a particle size distribution measuring apparatus according to the present invention includes the above-described optical analysis cell.

Such a particle size distribution measuring apparatus can obtain the same working effect as that of the above-described optical analysis cell.

Advantageous Effects of Invention

According to the present invention configured as described, completely differently from the conventional idea, without the use of any spacer, the viscoelasticity of a sample can be utilized to easily make the thickness of the sample uniform as well as making the pair of light transmitting plates parallel to each other.

DESCRIPTION OF EMBODIMENTS

In the following, one embodiment of the optical analysis cell according to the present invention will be described with reference to drawings.

Figure 2:
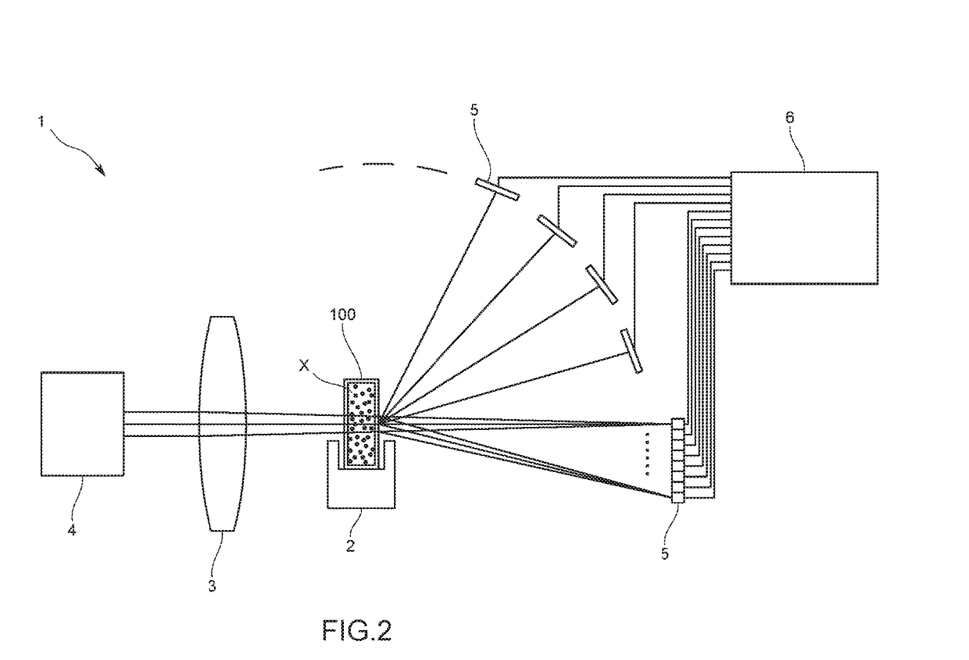
FIG. 2 is a schematic configuration diagram of a particle size distribution measuring apparatus applicable with an optical analysis cell in the present embodiment.

An optical analysis cell 100 according to the present embodiment is one that is used for, for example, as illustrated in FIG. 2, a particle size distribution measuring apparatus 1 adapted to, on the basis of the fact that a light intensity distribution with respect to the spread angle of diffracted/scattered light produced when radiating light to particles is determined by particle sizes in accordance with the MIE scattering theory, measure a particle size distribution by detecting the diffracted/scattered light.

Specifically, as illustrated in FIG. 2, the particle size distribution measuring apparatus 1 includes: the optical analysis cell 100 set in a cell holder 2; a laser device 4 as a light source adapted to radiate laser light to a sample X in the optical analysis cell 100 through a lens 3; multiple light detectors 5 adapted to detect the light intensities of diffracted/scattered lights produced by the radiation of the laser light at respective angles within a spread angle; and an arithmetic unit 6 adapted to receive light intensity signals outputted from the respective light detectors 5 to calculate the particle size distribution of particles contained in the sample X.

In the following, the optical analysis cell 100 as a distinctive part of the present invention will be described with reference to FIGS. 3 to 5.

The optical analysis cell 100 is one that contains the sample X having predetermined viscoelasticity, and in the present embodiment, used to analyze the sample X having a viscosity of, for example, 10 cP to 1000 cP, such as a sample formed by kneading magnetic particles such as magnetite into a viscoelastic solvent such as silicone oil or a slurry sample such as abrasive containing silica or tungsten.

Figure 3:
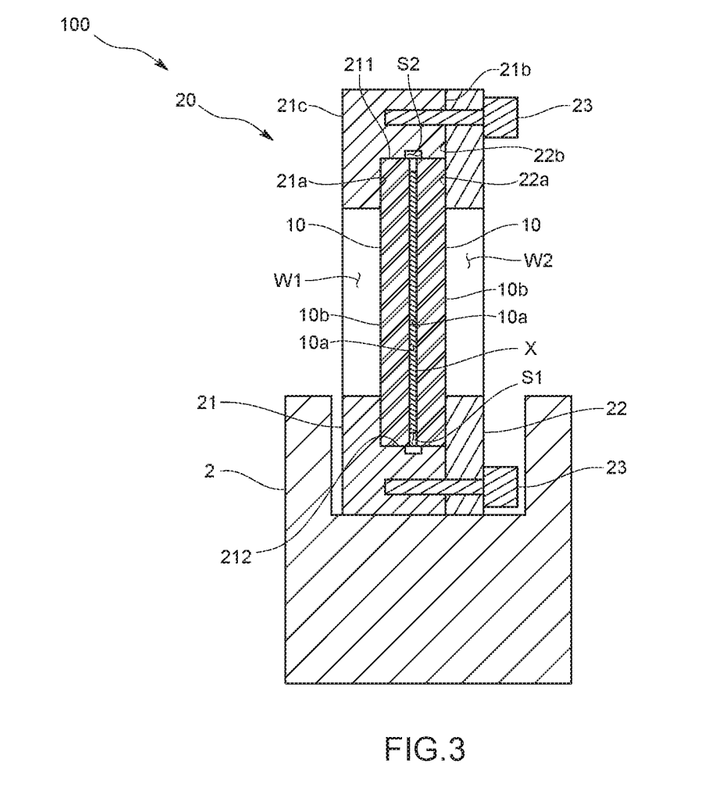
FIG. 3 is a diagram schematically illustrating the configuration of the optical analysis cell in the same embodiment.

Specifically, as illustrated in FIG. 3, the optical analysis cell 100 is configured to include: a pair of light transmitting plates 10 that sandwich and hold the sample X between mutually opposed inward surfaces 10a; and a distance fixing member 20 that fixes the separation distance between the inward surfaces 10a.

Figure 4:
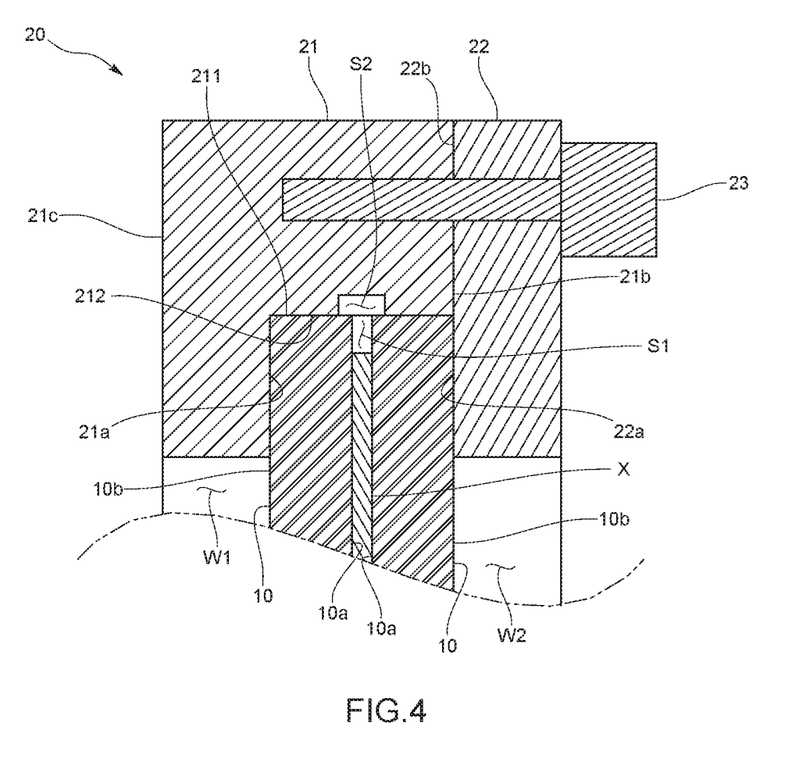
FIG. 4 is a partially enlarged view of the optical analysis cell in the same embodiment.

As illustrated in FIGS. 3 and 4, the respective light transmitting plates 10 are ones that allow the laser light radiated from the light source to transmit therethrough, and sandwich the sample X between at least unillustrated light transmitting areas of the inward surfaces 10a, through which the laser light transmits, as well as holding the sample X in a sample holding space S1 formed between the inward surfaces 10a.

Specifically, the respective light transmitting plates 10 are flat plates, of which the inward surfaces 10a and outward surfaces 10b facing the sides respectively opposite to the inward surface 10a are parallel to each other, and in the present embodiment, for example, rectangular-shaped flat glass plates having mutually the same shape.

In the present embodiment, the inward surfaces 10a are mutually opposed surfaces of the respective light transmitting plates 10, and the outward surfaces 10b are outer surfaces on the sides opposite to corresponding opposed surfaces.

Figure 5:
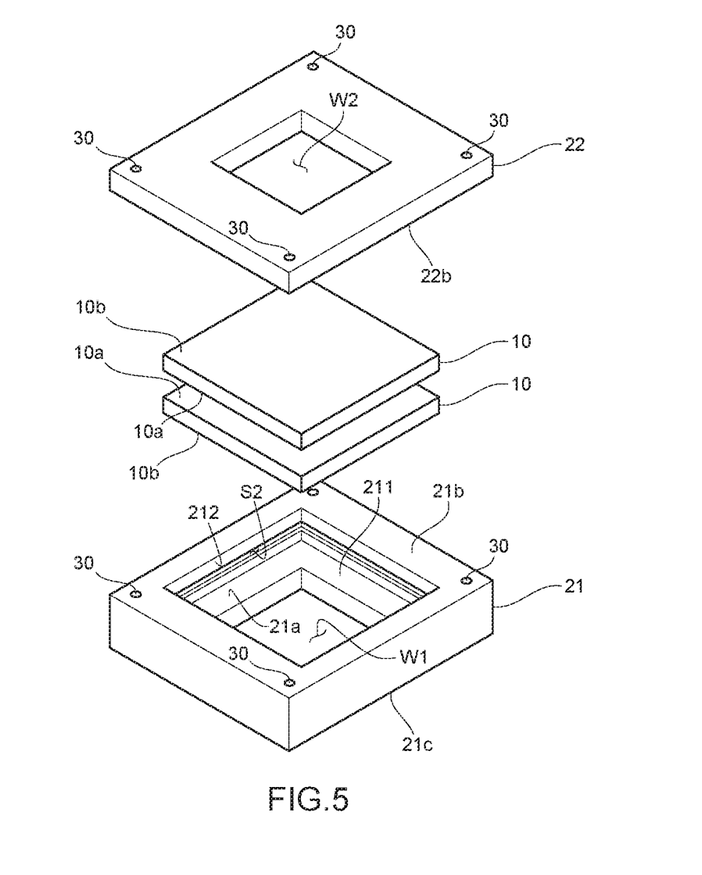
FIG. 5 is a perspective view schematically illustrating the configuration of the optical analysis cell in the same embodiment.

As illustrated in FIGS. 3 to 5, the distance fixing member 20 is one that has a pair of opposed surfaces 21a and 22a provided separately from each other by a predetermined distance, and utilizes the separation distance between the respective opposed surfaces 21a and 22a to fix the separation distance between the inward surfaces 10a to a predetermined setting size of, for example, 50 nm to 500 nm.

Specifically, the distance fixing member 20 includes: a first holding body 21 having the first opposite surface 21a; a second holding body 22 having the second opposite surface 22a; and connecting members 23 that connect the holding bodies 21 and 22 to each other, and sandwiches the pair of light transmitting plates 10 from outside between the first holding body 21 and the second holding body 22 to hold the pair of light transmitting plates 10.

The first holding body 21 is formed in, for example, a block body shape. Also, the first holding body 21 is formed with: a spot facing part 211 formed by hollowing a front surface 21b; and a light passing window W1 communicatively connecting a back surface 21c and the bottom surface of the spot facing part 211 to each other, and in the present embodiment, the bottom surface of the spot facing part 211 is formed as the first opposed surface 21a.

The spot facing part 211 is configured such that the pair of light transmitting plates 10 is fitted thereinto. Also, the depth size of the spot facing part 211 is slightly larger than the total size of the thicknesses of the respective light transmitting plates 10, and specifically, the spot facing part 211 is formed to have the depth size equal to the sum of the thicknesses of the respective light transmitting plates 10 and the above-describe setting size.

In the present embodiment, the inner peripheral surface of the spot facing part 211 is formed as a guide part 212 adapted to guide the respective light transmitting plates 10 when fitting the pair of the light transmitting plates 10 into the spot facing part 211, and the guide part 212 restricts the respective light transmitting plates 10 from moving in a planar direction.

The second holding body 22 is a flat plate lid body, of which the back surface 22b is superposed on the front surface 21b of the first holding body 21 to seal the spot facing part 211. Also, the second holding body 22 is formed with a light passing window W2 penetrating in a thickness direction, and part of the back surface 22b is formed as the second opposed surface 22a.

Note that in the configuration adapted to seal the spot facing part 211 as described above, if the amount of the sample X is too much, it may be impossible to block the spot facing part 211; however, in the present embodiment, a sample escape space S2 is formed around the sample holding space S1 formed between the inward surfaces 10a of the respective light transmitting plates 10.

In the present embodiment, the sample escape space S2 is a concave part formed in the above-described inner peripheral surface of the spot facing part 211, and specifically, the concave part is formed so as to open toward the sample holding space S1 and also communicatively connect to the sample holding space S1.

As described, in a state where the spot facing part 211 is sealed, i.e., in a state where the front surface 21b of the first holding body 21 and the back surface 22b of the second holding body 22 are in abutting contact with each other, the first opposed surface 21a and the second opposed surface 22a are parallel to each other. In the present embodiment, in this state, the holding bodies 21 and 22 are connected to each other by the connecting members 23.

The connecting members 23 are screws that are screwed into multiple screw holes 30 formed in the respective holding bodies 21 and 22, and in the present embodiment, the screw holes 30 are formed in the four corner parts of the respective holding bodies 21 and 22 to make it possible to apply uniform force to the respective holding bodies 21 and 22 when screwing the screws.

Subsequently, a method for assembling the above-described optical analysis cell 100 will be described.

First, the sample X is applied to, for example, one of the light transmitting plates 10, and the one light transmitting plate 10 is fitted into the spot facing part 211. Then, by superposing the other light transmitting 10 on the one light transmitting plate 10, the sample X is sandwiched between the pair of light transmitting plates 10. Note that in this series of processing step, the sample X may be applied to the other light transmitting plate 10.

After sandwiching the pair of light transmitting plates 10, only the sample X interposes between the respective light transmitting plates 10. Also, the pair of light transmitting plates 10 do not contact with each other, and only the sample X contacts with both of the inward surfaces 10a of the respective light transmitting plates 10.

Note that in this state, the separation distance between the outward surfaces 10b of the respective light transmitting plates 10 is longer than the depth of the spot facing part 211, and the other light transmitting plate 10 slightly protrudes from the spot facing part 211.

After that, the back surface 22b of the second holding body 22 is superposed on the front surface 21b of the first holding body 21 to seal the spot facing part 211, and the holding bodies 21 and 22 are connected to each other by the connecting members 23.

In addition, in the present embodiment, when the first holding body 21 and the second holding body 22 are connected to each other as described above, the inward surfaces 10a of the respective light transmitting plates 10 receive elastic force from the sample X. As a result, the respective light transmitting plates 10 are pressed outward, and also the outward surfaces 10b of the respective light transmitting plate 10 are pressed against opposed surfaces 21a and 22a of corresponding respective holding bodies 21 and 22.

In doing so, the respective outward surfaces 10b and corresponding respective opposed surfaces 21a and 22a closely contact with each other without any gap, and the separation distance between the inward surfaces 10a, i.e., the thickness of the sample X is fixed to the predetermined setting size defined by subtracting the thicknesses of the respective light transmitting plates 10 from the depth size of the spot facing part 211.

In the optical analysis cell 100 according to the present embodiment configured as described, since the elastic force of the sample X is utilized to bring the outward surfaces 10b of the respective light transmitting plates 10 into abutting contact with corresponding opposed surfaces 21a and 22a, which is completely different from the conventional idea using a spacer, only by assembling the optical analysis cell 100 as described above, the separation distance between the inward surfaces 10a of the respective light transmitting plates 10 can be fixed to the predetermined setting size.

This makes it possible to eliminate the need for delicate work, which may be required when interposing a spacer between the light transmitting plates 10, and easily make the thickness of the sample uniform as well as making the pair of light transmitting plates 10 parallel to each other.

Also, since the respective opposed surfaces 21a and 22a are provided separately from each other by the predetermined distance, by bringing the outward surfaces 10b of the respective light transmitting plates 10 in abutting contact with corresponding opposed surfaces 21a and 22a, the separation distance between the inward surfaces 10a can be surely fixed to the setting size defined by subtracting the thicknesses of the respective light transmitting plates 10 from the separation distance between the opposed surfaces 21a and 22a, and therefore the thickness of the sample can be accurately reproduced.

This makes it possible to, for example, make the sample thickness at the time of background measurement and the sample thickness at the time of sample measurement equal to each other, and thereby highly accurate measurement can be performed.

Further, since it is configured to simply sandwich the sample X between the pair of light transmitting plates 10, the thickness of the sample X can be made uniform by pressing and lengthening the sample X between the light transmitting plates 10, and also the pair of light transmitting plates 10 can be made parallel to each other. As a result, it is not necessary to accurately adjust the amount of the sample, which is also superior in practicality.

Although the light transmitting plates 10 are fragile, and required to be often replaced, the respective light transmitting plates 10 are flat glass plates, and therefore as the light transmitting plates 10, inexpensive general-purpose products can be used.

In addition, since the spot facing part 211 is sealed, the sample X can be prevented from unexpectedly leaking out of the optical analysis cell 100.

Further, since the sample escape space S2 is formed around the sample holding space S1, even if the amount of the sample X is too much, part of the sample X can flow into the sample escape space S2. As a result, the spot facing part 211 can be blocked, and also the thickness of the sample can be surely made uniform.

In terms of assembly work, since the depth size of the spot facing part 211 is larger than the total size of the thicknesses of the respective light transmitting plates 10, by fitting the pair of light transmitting plates 10 into the spot facing part 211 and then superposing the second holding body 22 on the light transmitting plates 10, the optical analysis cell 100 can be easily assembled.

Also, since the respective opposed surfaces 21a and 22a are made parallel to each other by bringing the front surface 21b of the first holding body 21 and the back surface 22b of the second holding body 22 into abutting contact with each other, only by assembling the optical analysis cell 100, the respective light transmitting plates 10 can be made parallel to each other.

Note that the present invention is not limited to the above-described embodiment.

Figure 6:
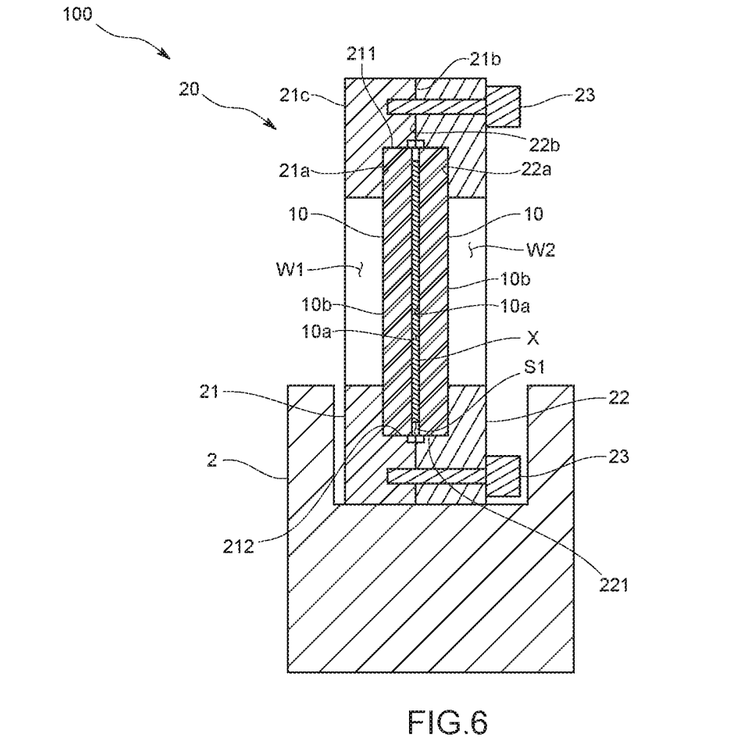
FIG. 6 is a diagram schematically illustrating the configuration of an optical analysis cell in a variation.

For example, in the above-described embodiment, the spot facing part 211 is formed in the first holding body 21. However, as illustrated in FIG. 6, both of the first and second holding bodies 21 and 22 may be formed with spot facing parts 211 and 221, respectively.

Specifically, the second holding member 22 is formed with the spot facing part 221 formed by hollowing the back surface 22b, and the bottom surface of the spot facing part 221 is formed as the second opposed surface 22a.

In this case, it is only necessary that the total size of the depths of the respective spot facing parts 211 and 221 respectively formed in the first holding body 21 and the second holding body 22 is configured to be larger than the total size of the thicknesses of the respective light transmitting plates 10.

Figure 7:
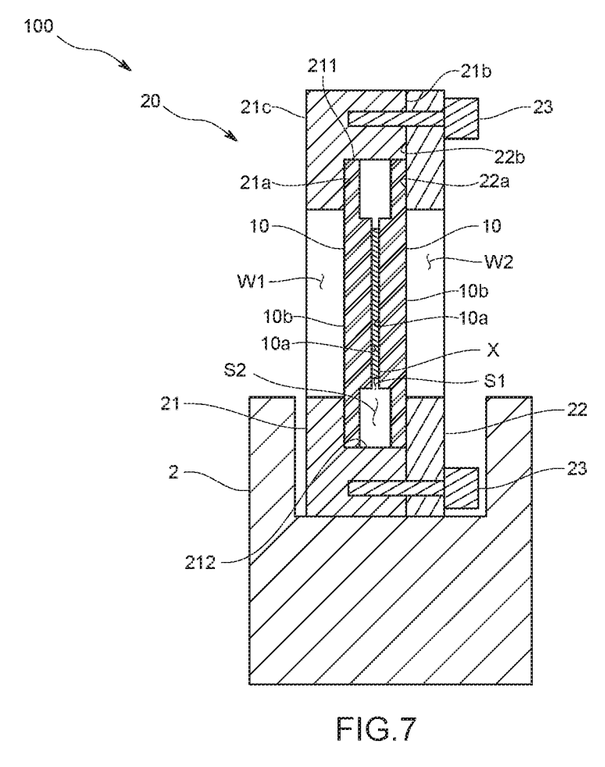
FIG. 7 is a diagram schematically illustrating the configuration of an optical analysis cell in another variation.

Also, in the above-described embodiment, the respective light transmitting plates 10 are flat plates. However, as illustrated in FIG. 7, it may be configured that the respective light transmitting plates 10 are formed in shapes in which parts of the mutually opposed surfaces protrude, and protruding surfaces are formed as the inward surfaces 10a sandwiching the sample X.

In addition, in the above-described configuration, between non-protruding parts of the opposed surfaces, the sample escape space S2 is formed.

Figure 8:
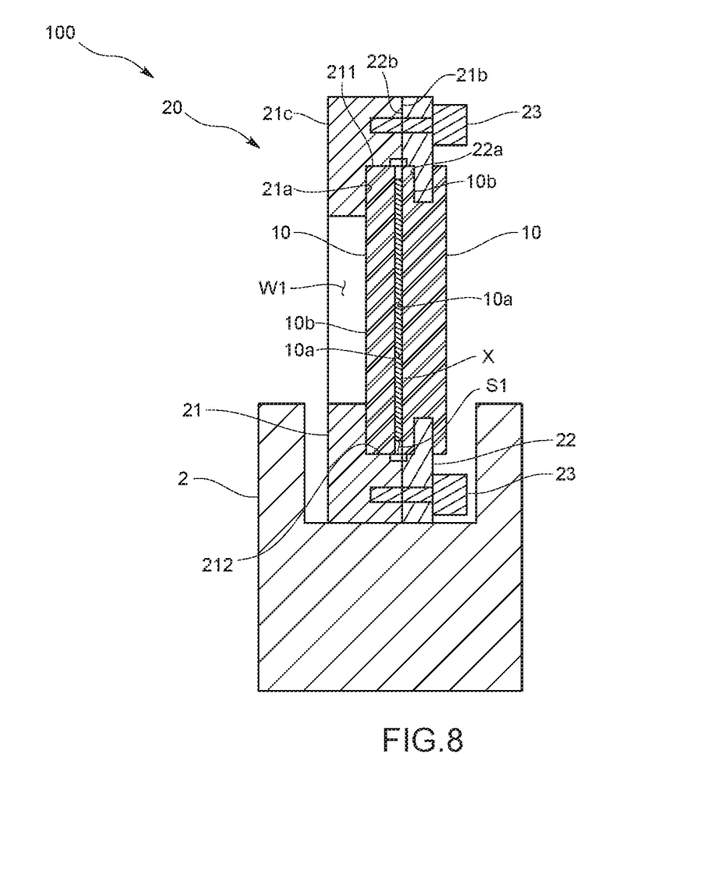
FIG. 8 is a diagram schematically illustrating the configuration of an optical analysis cell in still another variation.

Further, in the above-described embodiment, the outward surfaces 10b of the respective light transmitting plates 10 are the outer surfaces of the respective light transmitting plates 10. However, as illustrated in FIG. 8, a concave part is formed in the side peripheral surface of one of the light transmitting plates 10, and a surface of the inner peripheral surfaces of the concave part, which faces the side opposite to the sample X, may be defined as the outward surface 10b of the one light transmitting plate 10.

Figure 9:
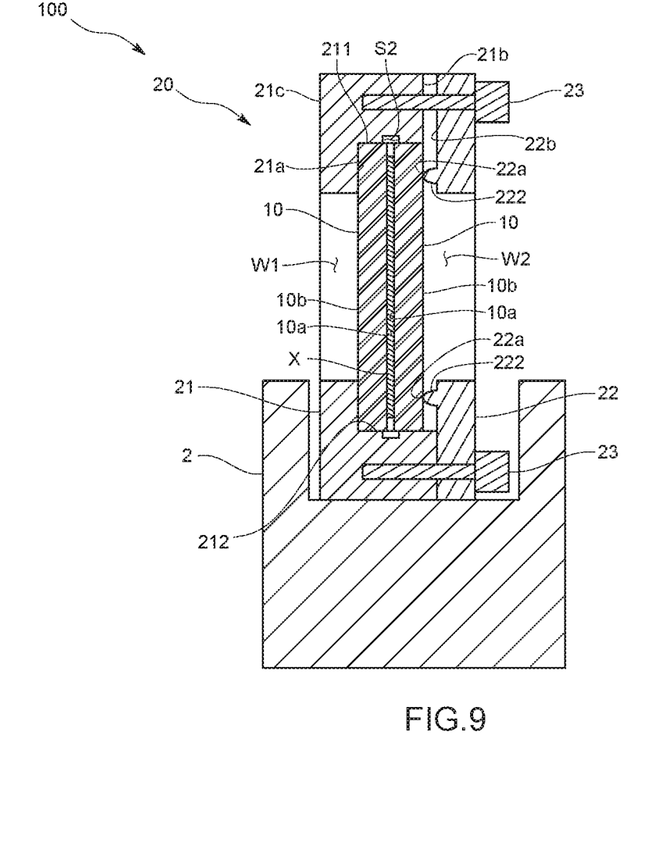
FIG. 9 is a diagram schematically illustrating the configuration of an optical analysis cell in yet another variation.

In addition, the second holding body 22 in the above-described embodiment is formed in a flat plate shape. However, as illustrated in FIG. 9, the second holding body 22 may be formed with multiple protrusion parts 222 on the back surface 22b thereof. In this case, the surfaces of the fore end parts of the respective protrusion parts 22 serve as opposed surfaces 22a.

Note that on the front surface 21b of the first holding body 21, protrusion parts may be formed.

Figure 10:
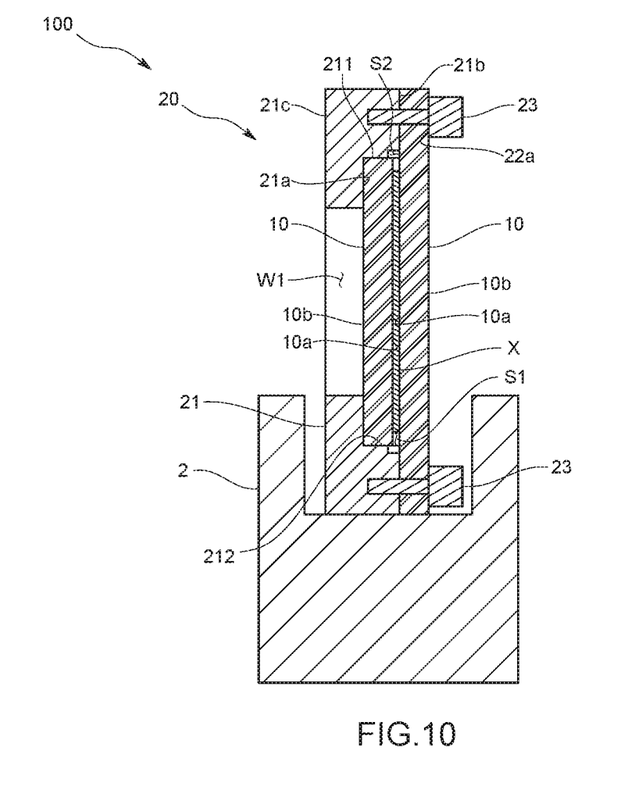
FIG. 10 is a diagram schematically illustrating the configuration of an optical analysis cell in yet still another variation.

Also, in the above-described embodiment, the pair of light transmitting plates 10 is sandwiched between the first holding body 21 and the second holding body 22. However, as illustrated in FIG. 10, it may be configured to use a resin-made light transmitting plate 10 formed with through-holes, and fix the resin-made light transmitting plate 10 to the first holding body 21 by the connecting members 23. This configuration makes it possible to eliminate the need for the second holding body in the above-described embodiment, and consequently make the optical analysis cell 10 compact. In addition, the light transmitting plate 10 is not required to be entirely made of resin. For example, it may be configured that the outer peripheral part of the light transmitting plate 10 is molded of metal and the through-holes are formed in the outer peripheral part, or the light transmitting plate 10 may be molded using glass.

In the above-described configuration, the pair of opposed surfaces 21a and 22a respectively correspond to the bottom surface of the spot facing part 211 formed in the first holding body 21, and fixing surfaces of the connecting members 23 fixing the light transmitting plate 10, and the outward surfaces 10b of the respective light transmitting plates 10 receive the elastic force from the sample X, and are thereby pressed against the bottom surface and the fixing surfaces.

On the other hand, in the above-described configuration, since the light transmitting plate 10 is directly fixed to the first holding body 21, the light transmitting plate 10 requires strength, and if the strength is insufficient, the light transmitting plate 10 may be broken. For this reason, from the perspective of easily assembling the optical analysis cell without breaking the light transmitting plate 10, as in the above-described embodiment, the configuration where the pair of light transmitting plates 10 is sandwiched between the first holding body 21 and the second holding body 22 is advantageous.

In addition, the particle size distribution measuring apparatus in the above-described embodiment is of a so-called diffraction/scattering type. However, the particle size distribution measuring apparatus may be of a dynamic light scattering type that is configured to radiate laser light to the sample in the optical analysis cell to analyze the fluctuation of scattered light caused by the Brownian motion of the particles in the sample, and thereby measure the particle size distribution.

Further, the optical analysis cell according to the present invention may be used for, in addition to the particle size distribution measuring apparatus, an optical analysis apparatus utilizing a method such as infrared spectroscopy.

Still further, the above-described embodiment is configured to fit the one light transmitting plate into the spot facing part, and then superpose the other light transmitting. However, it may be configured to sandwich the sample between the pair of light transmitting plates, and then fit the pair of light transmitting plates into the spot facing part.

Besides, it goes without saying that the present invention is not limited to the above-described embodiment or any of the above-described variations, but can be variously modified without departing from the scope thereof.

REFERENCE SIGNS LIST

100: Optical analysis cell
X: Sample
10: Light transmitting plate
10a: Inward surface
10b: Outward surface
20: Distance fixing member
21: First holding body
21a: First opposed surface
211: Spot facing part
22: Second holding body
22a: Second opposed surface

The invention claimed is:

1. An optical analysis cell, comprising:
a pair of light transmitting plates that sandwich and hold a sample having predetermined viscoelasticity between mutually opposed inward surfaces without a spacer that contacts both of the inward surfaces to fix a separation distance between the inward surfaces,
a distance fixing member having a pair of opposed surfaces provided separately from each other by a predetermined distance, wherein
the light transmitting plates are arranged between the pair of opposed surfaces such that when the sample having the predetermined viscoelasticity is disposed between the light transmitting plates, an elastic force of the sample is received by the light transmitting plates, and thereby outward surfaces on sides opposite to the inward surfaces of the light transmitting plates are pressed against the opposed surfaces of the distance fixing member to fix the separation distance between the inward surfaces, whereby the light transmitting plates do not contact each other when the light transmitting plates are pressed against the opposed surfaces of the distance fixing member.

2. The optical analysis cell according to claim 1, wherein around a sample holding space formed between the inward surfaces, a sample escape space is formed.

3. The optical analysis cell according to claim 2, wherein the sample escape space and the sample holding space form a closed space.

4. The optical analysis cell according to claim 1, wherein the respective light transmitting plates are flat plates.

5. The optical analysis cell according to claim 1, wherein the pair of opposed surfaces are provided parallel to each other.

6. The optical analysis cell according to claim 1, wherein the distance fixing member has:
a first holding body having a first one of the opposed surfaces;
a second holding body having a second one of the opposed surfaces; and
a connecting member that connects the holding bodies to each other.

7. The optical analysis cell according to claim 6, wherein at least one of the holding bodies has a guide part that guides an outward surface of a light transmitting plate to a corresponding opposed surface.

8. The optical analysis cell according to claim 6, wherein at least one of the holding bodies is formed with a recess having a bottom surface forming one of the opposed surfaces.

9. A particle size distribution measuring apparatus comprising the optical analysis cell according to claim 1.

* * * * *